US012246125B2

(12) United States Patent
Locke et al.

(10) Patent No.: US 12,246,125 B2
(45) Date of Patent: Mar. 11, 2025

(54) ABDOMINAL DRESSING WITH USER SELECTION OF FASCIAL CLOSURE FORCE PROFILE

(71) Applicant: Solventum Intellectual Properties Company, Maplewood, MN (US)

(72) Inventors: Christopher B. Locke, Bournemouth (GB); Timothy Mark Robinson, Wimborne (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 230 days.

(21) Appl. No.: 17/258,360

(22) PCT Filed: Jul. 9, 2019

(86) PCT No.: PCT/US2019/040930
§ 371 (c)(1),
(2) Date: Jan. 6, 2021

(87) PCT Pub. No.: WO2020/014178
PCT Pub. Date: Jan. 16, 2020

(65) Prior Publication Data
US 2021/0268166 A1    Sep. 2, 2021

Related U.S. Application Data

(60) Provisional application No. 62/697,181, filed on Jul. 12, 2018.

(51) Int. Cl.
| *A61M 1/00* | (2006.01) |
| *A61F 13/05* | (2024.01) |
| *A61F 13/14* | (2006.01) |

(52) U.S. Cl.
CPC ............. *A61M 1/916* (2021.05); *A61F 13/05* (2024.01); *A61F 13/148* (2013.01); *A61M 1/915* (2021.05)

(58) Field of Classification Search
CPC ........ A61M 1/916; A61M 1/915; A61M 1/00; A61F 13/00068; A61F 13/148; A61F 13/00; A61F 13/14; B26F 1/00
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion in International Application No. PCT/US2019/040930 mailed on Sep. 27, 2019.

(Continued)

*Primary Examiner* — Kai H Weng
*Assistant Examiner* — Alessandro R Del Priore

(57) ABSTRACT

A negative pressure wound therapy (NPWT) device for a deep abdominal wound. The compressive component includes a body having a first compressive profile. The body includes a plurality of removable portions of the material. The plurality of removable portions are configured to be selectively removed to form a pattern of voids to transform the first compressive profile of the body into a second compressive profile of the body based on the pattern of voids. The pattern of voids includes at least one void.

8 Claims, 8 Drawing Sheets

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,328,450 A * | 7/1994 | Smith ................ A61F 13/512 |
| | | 602/41 |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 9,421,132 B2 | 8/2016 | Dunn |
| 9,962,295 B2 | 5/2018 | Dunn et al. |
| 10,117,782 B2 | 11/2018 | Dagger et al. |
| 10,130,520 B2 | 11/2018 | Dunn et al. |
| 10,159,771 B2 | 12/2018 | Hartwell et al. |
| 10,179,073 B2 | 1/2019 | Hartwell et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0161937 A1 | 7/2007 | Aali |
| 2011/0213287 A1* | 9/2011 | Lattimore ................ A61M 1/90 |
| | | 604/319 |
| 2011/0224630 A1* | 9/2011 | Simmons .............. A61M 1/916 |
| | | 604/317 |
| 2011/0319804 A1* | 12/2011 | Greener ................ A61F 15/001 |
| | | 83/13 |
| 2014/0163491 A1 | 6/2014 | Schuessler et al. |
| 2015/0080788 A1 | 3/2015 | Blott et al. |
| 2015/0174284 A1* | 6/2015 | Payne ................ B32B 38/0004 |
| | | 604/368 |
| 2016/0022885 A1* | 1/2016 | Dunn .................... A61F 13/022 |
| | | 604/319 |
| 2016/0166744 A1* | 6/2016 | Hartwell .......... A61F 13/00021 |
| | | 604/319 |
| 2017/0209641 A1* | 7/2017 | Mercer .................... A61M 1/85 |
| 2018/0222077 A1* | 8/2018 | Cecchetto ................ B26F 1/20 |
| 2019/0105202 A1 | 4/2019 | Dunn et al. |
| 2019/0209383 A1 | 7/2019 | Hartwell et al. |
| 2019/0231599 A1 | 8/2019 | Dagger et al. |
| 2019/0231945 A1 | 8/2019 | Hartwell et al. |
| 2019/0262182 A1* | 8/2019 | Collinson ............ A61M 1/915 |
| 2019/0336345 A1* | 11/2019 | Bannwart ............ A61M 1/915 |
| 2021/0137743 A1* | 5/2021 | Hartwell .................. A61F 13/00 |
| 2021/0137746 A1* | 5/2021 | Dutta ................ A61F 13/0216 |

(56) References Cited

U.S. PATENT DOCUMENTS

FOREIGN PATENT DOCUMENTS

| AU | 755496 B2 | 12/2002 |
|---|---|---|
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2015/008054 A1 | 1/2015 |
| WO | WO-2017/063036 A1 | 4/2017 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A.C.® Therapy Clinical Guidelines: A Reference Source for Clinicians; Jul. 2007.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

(56) References Cited

OTHER PUBLICATIONS

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

* cited by examiner

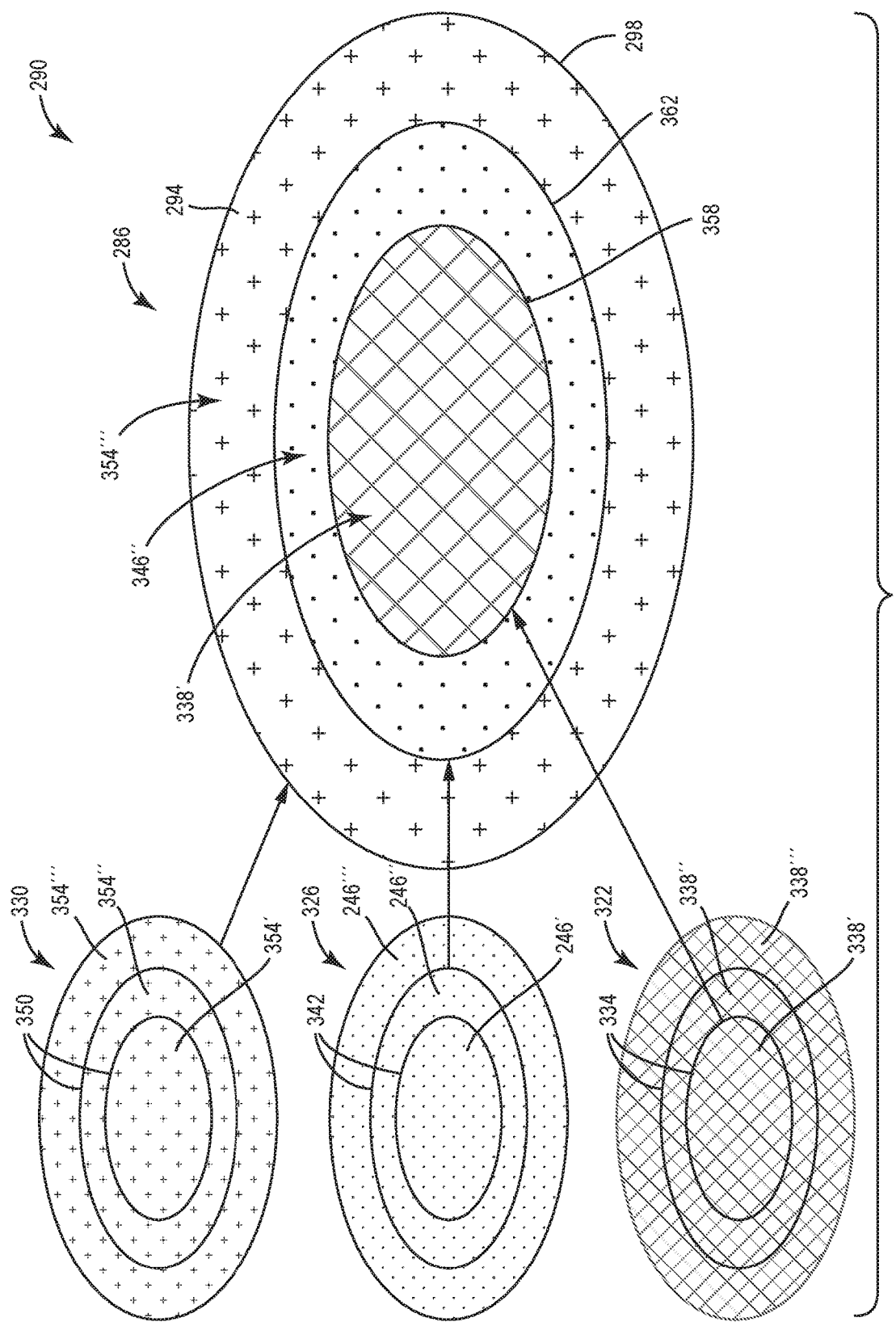

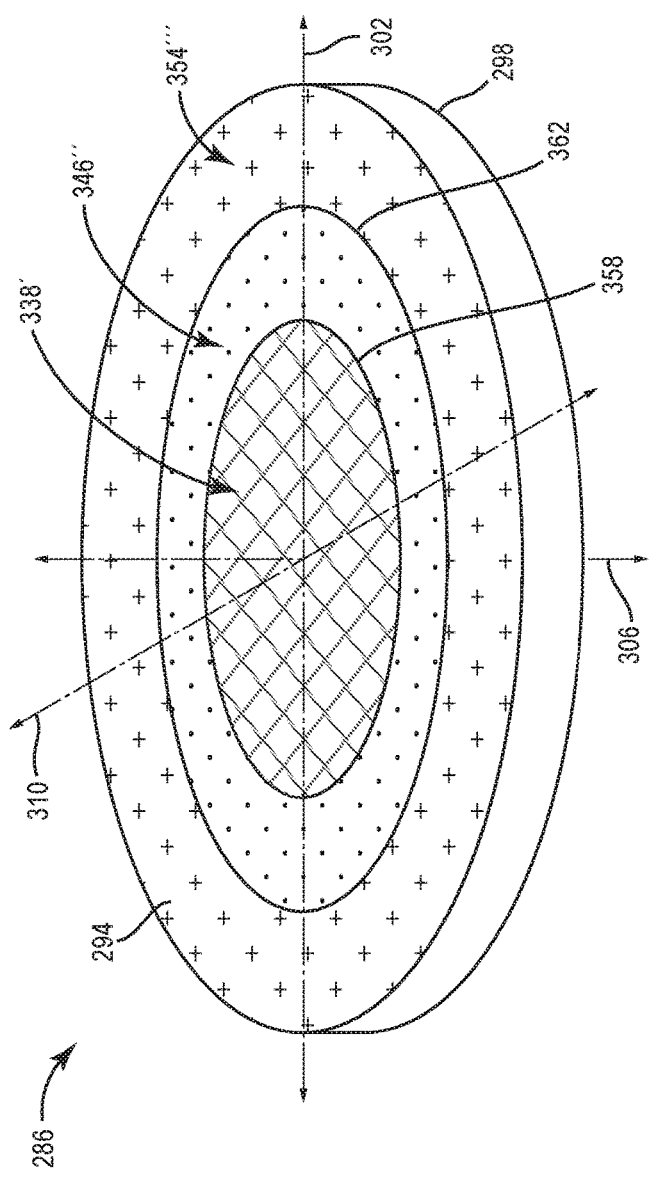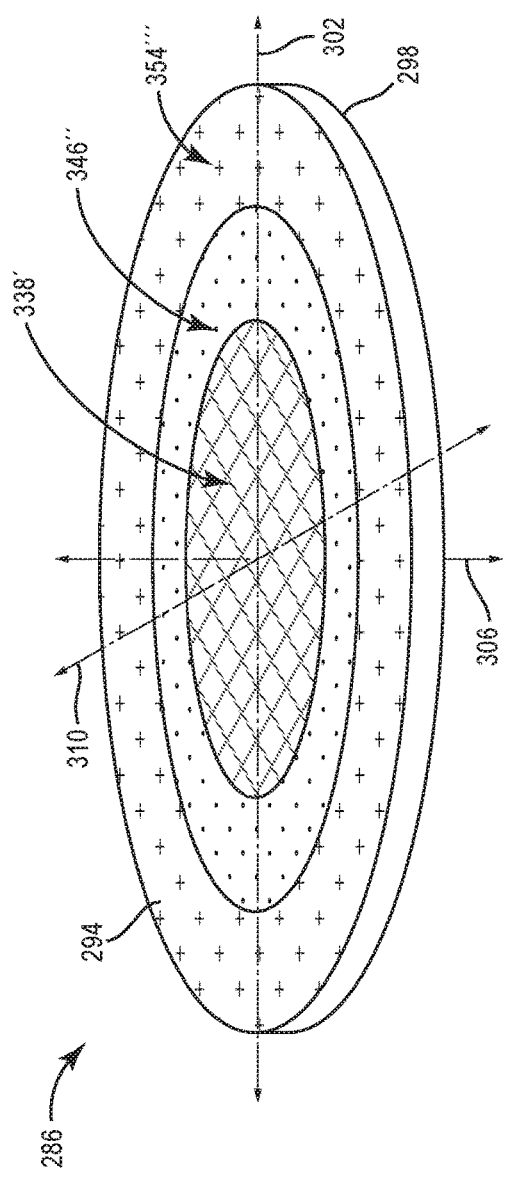

ABDOMINAL DRESSING WITH USER SELECTION OF FASCIAL CLOSURE FORCE PROFILE

CROSS-REFERENCE TO RELATED APPLICATIONS

This application claims the benefit of priority to international patent application number PCT/US2019/040930, filed on Jul. 9, 2019, which claims the benefit of priority to U.S. Provisional Application No. 62/697,181, filed on Jul. 12, 2018, the complete disclosures of which are hereby incorporated herein by reference in their entireties.

BACKGROUND

The present disclosure relates generally to a wound therapy system, and more particularly to a compressive component of a wound treatment system configured to provide negative pressure wound therapy to a fascial incision in an deep abdominal incision.

Negative pressure wound therapy is a type of wound therapy that involves applying a negative pressure to a wound site to promote wound healing. NPWT applies negative pressure to the wound to drain fluids from the wound as the wound heals. NPWT can be used to treat deep abdominal wounds due to abdominal laparotomies, which are used to gain access to the abdominal cavity for surgery and/or to relieve intra-abdominal pressure by allowing the bowels to expand. Such deep abdominal wounds require cutting of the fascial layer, which is a thin, fibrous layer of tissue located beneath the abdominal muscles that holds the abdominal contents (e.g., internal organs and the bowels) together. In some instances, the laparotomy incision is not immediately closed, resulting in an "open abdomen." Under such conditions, the fascia can retract laterally toward the patient's paracolic gutters (e.g., open space on the sides of the abdominal cavity), which can make it difficult to secure the cut ends of the fascial layer together (e.g., with staples or sutures) after surgery. Staples and/or sutures are currently used to hold the cut ends of the fascia together under the open abdomen conditions. It may be beneficial to provide an improved wound therapy system for closing deep abdominal incisions.

SUMMARY

One implementation of the present disclosure is a method of customizing a compressive profile of a negative pressure wound therapy (NPWT) dressing for a deep abdominal wound. The method includes providing a body formed of a material having a first compressive profile. The body includes a plurality of removable portions of the material. The method further includes selectively removing at least one of the plurality of removable portions of the material to form a pattern of one or more voids. The pattern of one or more voids is configured to transform the first compressive profile of the body to a second compressive profile. The second compressive profile based on the pattern of one or more voids.

Another implementation of the present disclosure is a negative pressure wound therapy (NPWT) device for a deep abdominal wound. The compressive component includes a body having a first compressive profile. The body includes a plurality of removable portions of the material. The plurality of removable portions are configured to be selectively removed to form a pattern of voids to transform the first compressive profile of the body into a second compressive profile of the body based on the pattern of voids. The pattern of voids includes at least one void.

Another implementation of the present disclosure is a method for forming a negative pressure wound therapy (NPWT) dressing for a deep abdominal wound. The method includes selecting a first compressive material having a first compression ratio. The first compressive material includes a first pattern of concentric perforations configured to form a plurality of first detachable compressive component segments. The method further includes selecting a second compressive material having a second compression ratio different than the first compression ratio. The second compressive material includes a second pattern of concentric perforations configured to form a plurality of second detachable segments. The method further includes forming the composite compressive component by detaching at least one first compressive component segment from the first compressive material and detaching at least one second compressive component segment from the second compressive material. The at least one second compressive component segment includes an opening configured for receiving the at least one first compressive component segment therein. The method of forming the composite compressive component further includes positioning the at least one first compressive component segment within the opening of the second compressive component segment to form the composite compressive component.

Another implementation of the present disclosure is a system for forming a negative pressure wound therapy (NPWT) dressing for treating a deep abdominal wound. The system includes a first compressive material having a first compression ratio. The first compressive material includes a first pattern of concentric perforations configured to form at least a first detachable compressive component segment. The system further includes a second compressive material having a second compression ratio different than the first compression ratio. The second compressive material includes a second pattern of concentric perforations configured to form at least a second detachable compressive component segment. The second detachable compressive component segment includes an opening configured to receive the first detachable compressive component segment to form the composite compressive component.

Another implementation of the present disclosure includes a negative pressure wound therapy (NPWT) dressing. The composite compressive component has a compression profile including a central portion formed from a first compressive material having a first compression ratio, and a first ring portion substantially surrounding the central portion. The first ring portion is formed from a second compressive material having a second compression ratio. Upon application of a negative pressure a lateral contraction of the ring portion is greater than a lateral contraction of the central portion.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE DRAWINGS

FIG. 7 is a front view of a composite abdominal dressing system for use with the wound therapy system of FIG. 1 according to an exemplary embodiment.

FIG. 8 is a perspective view of the composite abdominal dressing of FIG. 7.

FIG. 9 is a perspective view of the composite abdominal dressing of FIG. 7 under negative pressure.

DETAILED DESCRIPTION

Overview

Figure 1:
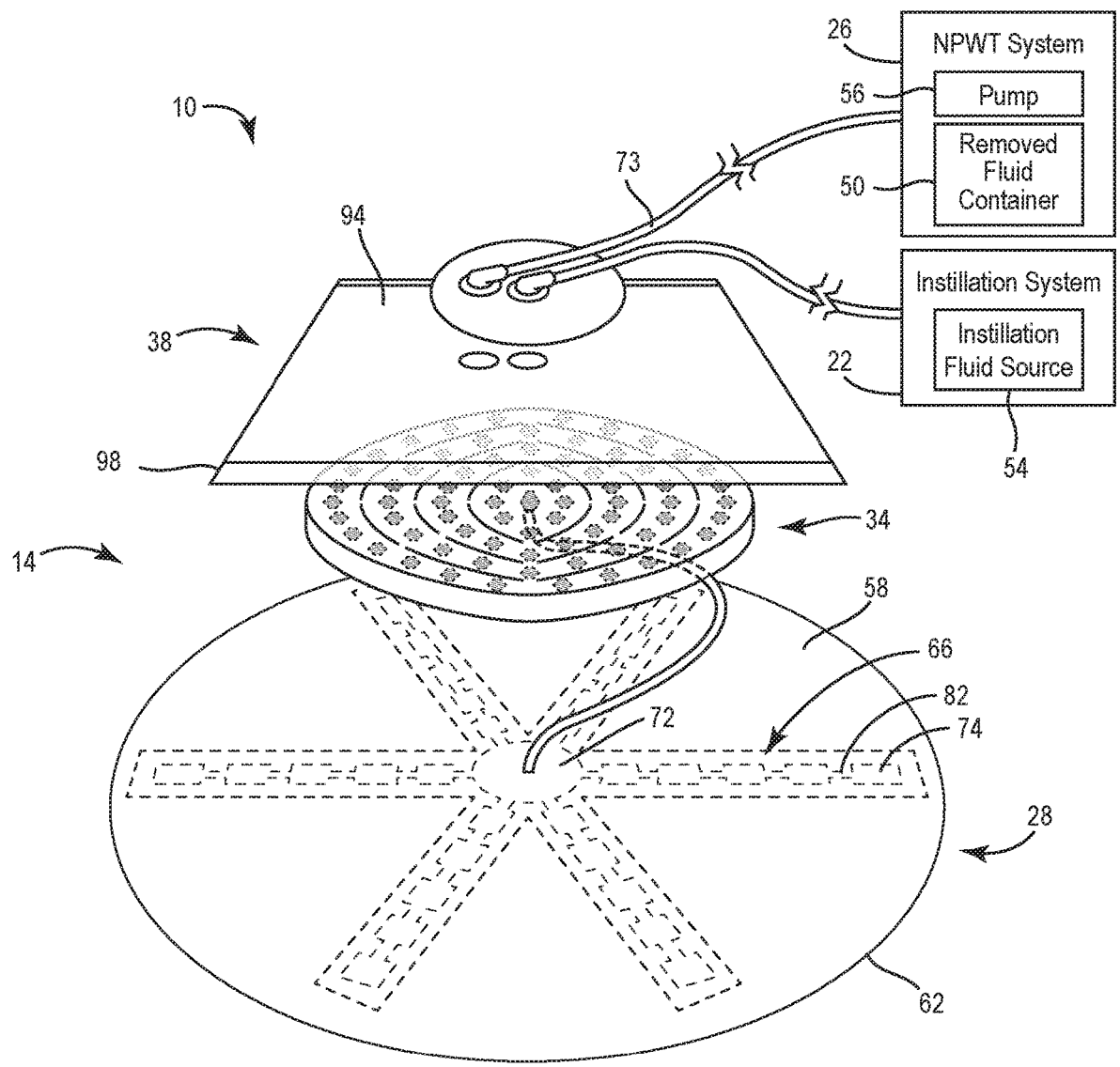
FIG. 1 is an exploded view of a wound therapy system for use with a deep abdominal wound according to an exemplary embodiment.

Referring generally to the FIGURES, a wound therapy system for treating a deep abdominal wound and/or an open abdomen is shown, according to various embodiments. The phrase "deep abdominal wound" refers to an abdominal incision that includes an incision in the fascial layer to access the abdominal cavity. The fascial layer is a layer of tissue that surrounds and supports the abdominal contents (e.g., the bowels and the internal organs). The phrase "open abdomen" refers to conditions in which a deep abdominal wound is left open (e.g., the abdominal incision is not resealed) for a period of time. For example, the abdomen may be left open to accommodate swelling of the bowels and/or other abdominal contents (e.g., internal organs). The abdomen may also be left open in conditions in which further surgery in the abdominal cavity is required. More specifically, the wound therapy system is for treating open abdominal incisions that include an incision in the fascial layer. The wound therapy system is configured to engage the fascial layer proximate the fascial incision and rejoin the cut ends of the fascial layer, preventing retraction of the cut ends of fascial later during the open abdomen conditions.

The wound therapy system includes a plurality of layers, including a visceral protective layer, a compressive component, and a sealing layer. The wound therapy system can be used with a negative pressure wound therapy (NPWT) system and/or an installation system. The visceral protective layer is positioned within the abdominal cavity and wrapped around the bowels and internal organs. The compressive component is positioned within the abdominal cavity and is configured to contract laterally and/or radially under negative pressure to pull the cut ends of the fascial layer together. The sealing layer is configured to be affixed to a patient's skin surrounding an abdominal incision and to provide a sealed space (e.g., in the open abdomen).

More specifically, the compressive component is configured to overlie a fascial incision formed proximate a bottom of the abdominal incision. The compressive component has a generally elliptical shape to conform to a shape of the open abdominal incision. The compressive component 46 can be made from a porous and permeable foam-like material and can be adapted to wick fluid (e.g. exudate) from the wound and can include in-molded manifold structures for distributing negative pressure throughout the wound dressing during NPWT treatments. In some cases, the facial incision is non-uniformly shaped. For example, the fascial incision may have a substantially teardrop shape, in which one end of the incision is wider than another end. In such conditions, it can be desirable to customize the compressive component to provide different amounts of lateral compression, and therefore different amounts of lateral closure forces, to different portions of the fascial incision based on the shape of the fascial incision In some embodiments, the compressive component includes a plurality of removable segments that that can be selectively and individually removed from the compressive component to form a plurality of voids. A pattern and/or a position of the plurality of voids can change a compressive profile of the compressive component. For example, the compressive component can have a first compressive profile in which none of the removable portions have been remove is generally uniform over the compressive component. Removing at least one of the removable components changes the compressive profile from the first compressive profile to a second compressive profile, in which at least a portion of the compressive profile is non-uniform.

In some embodiments, the compressive component can be a composite compressive component in which the compressive component is formed from different concentric segments having different densities and/or different material properties that cause the composite compressive component to provide different amounts of lateral compressive forces to the fascial incision under negative pressure conditions.

Additional features and advantages of the wound therapy system are described in detail below.

Wound Therapy System

Referring to FIG. 1, a section view of a wound therapy system 10 is shown, according to an exemplary embodiment. In the illustrated embodiment, the wound therapy system is configured to treat the abdominal cavity and is discussed in the context of treating an open abdomen. The wound therapy system 10 can be used to treat an "open abdomen" condition, in which a deep abdominal wound is left open for a period of time. The components described herein may be used in different configurations of instillation therapy systems and/or negative pressure wound therapy (NPWT) systems. The phrase "negative pressure" means a pressure less than an ambient or atmospheric pressure.

In various embodiments, the wound therapy system 10 can be used to treat a deep abdominal incision. The wound therapy system 10 includes a wound dressing 14, an instillation system 22, and a NPWT system 26. The wound dressing 14 includes an abdominal treatment device 28, a negative pressure manifold or compressive component 34, and a sealing member 38. The wound dressing 14 is intended for engagement with a treatment site of a patient, such as an abdominal cavity of a patient. The wound therapy system 10 can be used with the NPWT system 26 and/or the instillation system 22. The NPWT system 26 may include a negative pressure source 46, such as a pump, and a fluid collection chamber 50. The instillation system 22 may include an instillation fluid source 54. In some embodiments, the instillation system 22 may include an installation pump 56.

The compressive component 34 is shaped to be positioned within at least a portion of the abdominal incision, such as an incision formed as part of a vertical laparotomy. The compressive component is configured to overlie a fascial incision formed proximate a bottom of the abdominal incision 22. Accordingly, the compressive component 34 is shaped to conform to a shape of the open abdominal incision 22. For example, as shown in the Figures, the compressive component 34 has a generally elliptical shape.

The Abdominal Treatment Device

Referring to FIG. 1, the abdominal treatment device 28 is shown to include a first layer 58, a second layer 62, and a foam spacer 66. The second layer 62 faces the abdominal contents and is generally opposite the first layer 58. The foam spacer 66 includes a first surface 68 and a second, abdominal contents-facing surface 70. The foam spacer 66 includes a hub 72 and a plurality of leg members 74 that extend generally radially from the hub 72. The foam spacer 66 is generally in fluid communication with a negative pressure conduit 73 to receive negative pressure from the negative pressure source 46 and to receive fluids flowing from the treatment site towards the negative pressure source 46. The plurality of elongate leg members 74 are configured to distribute negative pressure throughout the treatment site. The first layer 58 and the second layer 62 encapsulate the leg members 74, the hub 72, and the intervening space between adjacent leg members 74. In the illustrated embodiment, the hub 72 and the plurality of leg members 74 are made of a material that is substantially hydrophobic and configured for fluid flow under substantially atmospheric pressure conditions and under negative pressure conditions. In some embodiments, the hub 72 and the plurality of leg members 74 are made of a reticulated foam, such as the reticulated foam described below with respect to the compressive component 34. In some embodiments, the leg members 74 may be cut to accommodate relatively small wounds. The first layer 58 and the second layer 62 of the abdominal treatment device 28 can made of a material that is fluid-impermeable and intended to not irritate the patient's fascia and internal organs. The abdominal treatment device 28 may include a plurality of fenestrations 78 (e.g., negative pressure inlets) for distribution of negative pressure by the plurality of leg members 74 and/or to permit fluid to flow into the plurality of leg members 74 and/or the space between the plurality of leg members 74 and the layers 58, 62. The fenestrations 78 may include through-holes, slits, or linear cuts. The fenestrations 78 may be circular, rectangular, polygonal, or be any other shape in cross-section.

The Compressive Component

Referring to FIG. 1, the compressive component 34 is shown to include a first surface 82 and a second, abdominal contents-facing surface 86 opposite the first surface 82. When the compressive component 34 is applied to the treatment site, the first surface 82 faces away from the abdominal contents, whereas the second surface 86 faces toward the abdominal contents. In some embodiments, the first surface 82 of the compressive component 34 contacts the second surface 86 of the sealing member 38. The compressive component 34 is adapted to wick fluid (e.g. exudate) from the wound and includes in-molded manifold structures for distributing negative pressure throughout the compressive component 34 during negative pressure wound therapy treatments. The compressive component 34 is made from a material that allows fluid and/or negative pressure to pass from between at least a first portion of the compressive component 34 and a second portion of the compressive component 34. In some embodiments, the compressive component 34 may include in-molded flow channels or pathways that can distribute the fluids provided to and removed around the manifold. In some embodiments, the in-molded flow channels or pathways can be formed by the cells in a porous foam material. The compressive component 34 can be a manifold configured to allow fluid to pass from at least a first portion of the compressive component 34 to at least a second portion of the compressive component 34.

The compressive component 34 can be made from a porous and permeable foam-like material and, more particularly, a reticulated, open-cell polyurethane or polyether foam that allows good permeability of wound fluids while under a reduced pressure. One such foam material that has been used is the VAC® Granufoam® material that is available from Kinetic Concepts, Inc. (KCI) of San Antonio, Tex. Any material or combination of materials might be used for the compressive component 34 provided that the compressive component 34 is operable to distribute the reduced pressure and provide a distributed compressive force along the treatment site.

The reticulated pores of the Granufoam® material that are in the range from about 400 to 600 microns, are preferred, but other materials may be used. The density of the absorbent layer material, e.g., Granufoam® material, is typically in the range of about 1.3 lb/ft$^3$-1.6 lb/ft$^3$ (20.8 kg/m$^3$-25.6 kg/m$^3$). A material with a higher density (smaller pore size) than Granufoam® material may be desirable in some situations. For example, the Granufoam® material or similar material with a density greater than 1.6 lb/ft$^3$ (25.6 kg/m$^3$) may be used. As another example, the Granufoam® material or similar material with a density greater than 2.0 lb/ft$^3$ (32 kg/m$^3$) or 5.0 lb/ft$^3$ (80.1 kg/m$^3$) or even more may be used. The more dense the material is, the higher compressive force that may be generated for a given reduced pressure. If a foam with a density less than the tissue at the tissue site is used as the absorbent layer material, a lifting force may be developed. In one illustrative embodiment, a portion, e.g., the edges, of the wound dressing may exert a compressive force while another portion, e.g., a central portion, may provide a lifting force.

The compressive component 34 material may be a reticulated foam that is later felted to thickness of about one third (⅓) of the foam's original thickness. Among the many possible absorbent layer materials, the following may be used: Granufoam® material or a Foamex® technical foam (www.foamex.com). In some instances it may be desirable to add ionic silver to the foam in a microbonding process or to add other substances to the compressive component 34 material such as antimicrobial agents. In some instances, it may be desirable to add active and/or time-release therapeutic compounds to the compressive component 34 material. The compressive component 34 material may be isotropic or anisotropic depending on the exact orientation of the compressive forces that are desired during the application of reduced pressure. The compressive component 34 material may also be a bio-absorbable material.

In some embodiments, the compressive component 34 can be made of Granufoam®, felted foam, a three-dimensional textile material such as BallTex, a welded film with hexagonal three-dimensional construction, a non-woven layer, a vacuum-formed structure, layers of vacuum formed film with air bubbles and/or other positive-shaped structures, an injection-molded polymer, or any other material in which the closure force in the lateral direction may be modulated through the selective removal of the material.

In embodiments including the three-dimensional textile material, the thickness, weave pattern, and/or perforation pattern can change the collapse of the material, allowing the force, the shape, and the compressive profile of the three-dimensional textile to be customized.

The Sealing Member

Referring again to FIG. 1, the sealing member 38 is shown to include a first surface 94 and a second, wound-facing, surface 98 opposite the first surface 94. When the wound therapy system 10 is applied to a wound, the first surface 94 faces away from the wound, whereas the second surface 98 faces toward the wound. As is shown in FIG. 1, at least a perimeter of the second surface 98 includes an adhesive. The adhesive is intended to secure sealing member 38 to the patient's skin and to form a fluid-tight seal about the incision. The sealing member 38 also provides a barrier to passage of microorganisms through the wound therapy system 10.

In some embodiments, the sealing member 38 is an elastomeric material or may be any material that provides a fluid seal. "Fluid seal" means a seal adequate to hold pressure at a desired site given the particular reduced-pressure subsystem involved. The term "elastomeric" means having the properties of an elastomer and generally refers to a polymeric material that has rubber-like properties. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, thermoplastic polyurethane (TPU), and silicones. As non-limiting examples, the sealing member 38 may be formed from materials that include a silicone, 3M Tegaderm® drape material, acrylic drape material such as one available from Avery, or an incise drape material. In some embodiments, the sealing member 38 may be at least partially transparent to facilitate viewing of the wound therapy system 10 through the sealing member 38 as described in greater detail below.

The sealing member 38 may be substantially impermeable to liquid and substantially permeable to water vapor. In other words, the sealing member 38 may be permeable to water vapor, but not permeable to liquid water or wound exudate. This increases the total fluid handling capacity (TFHC) of wound therapy system 10 while promoting a moist wound environment. In some embodiments, the sealing member 38 is also impermeable to bacteria and other microorganisms. In some embodiments, the sealing member 38 is configured to wick moisture from the compressive component 34 and distribute the moisture across the first surface 94. In some embodiments, the adhesive applied to the second surface 98 of the sealing member 38 is moisture vapor transmitting and/or patterned to allow passage of water vapor therethrough.

Compressive Component

Figure 2:
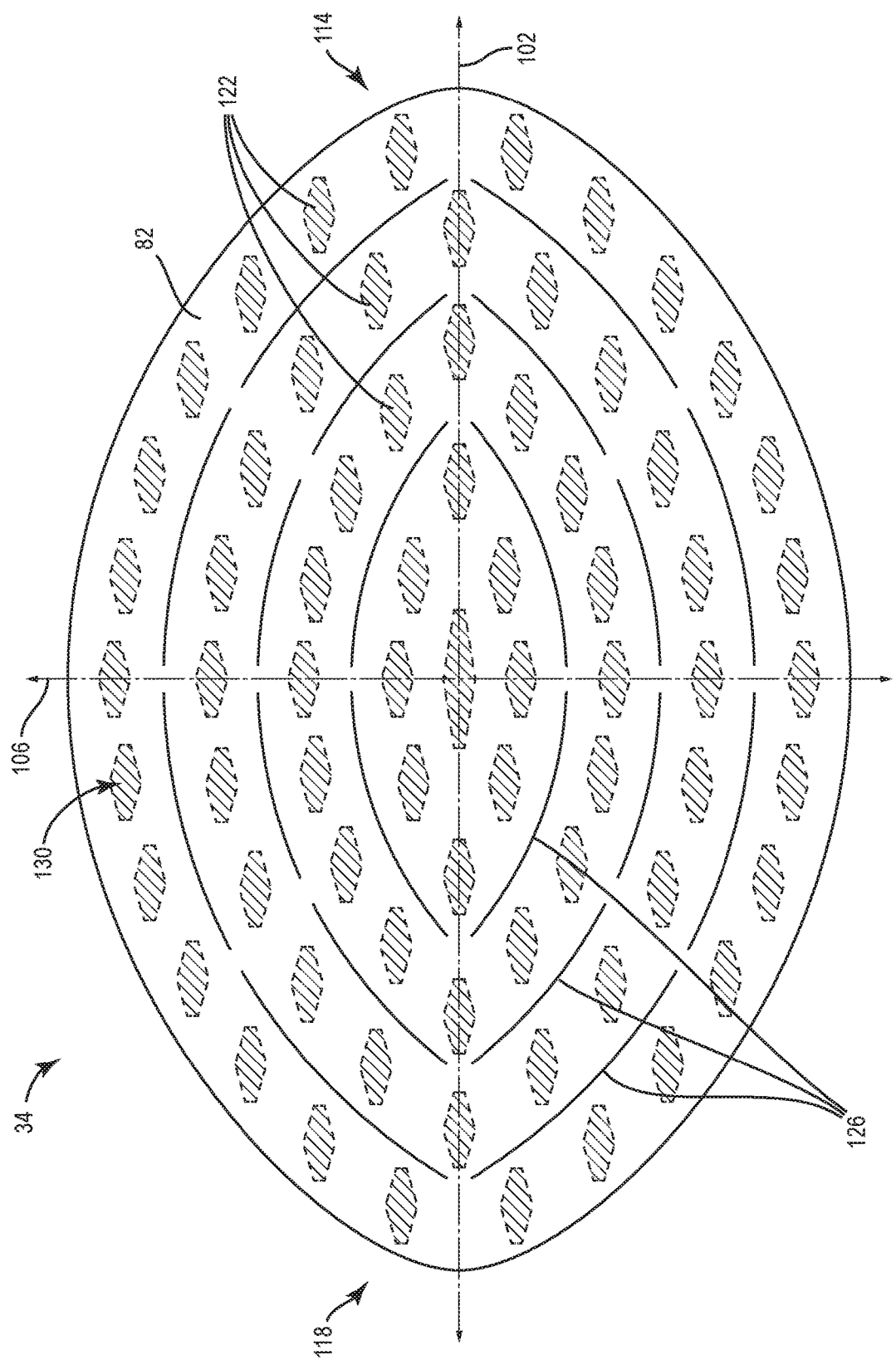
FIG. 2 is a front view of an abdominal dressing the wound therapy system of FIG. 1 according to an exemplary embodiment.
Figure 3:
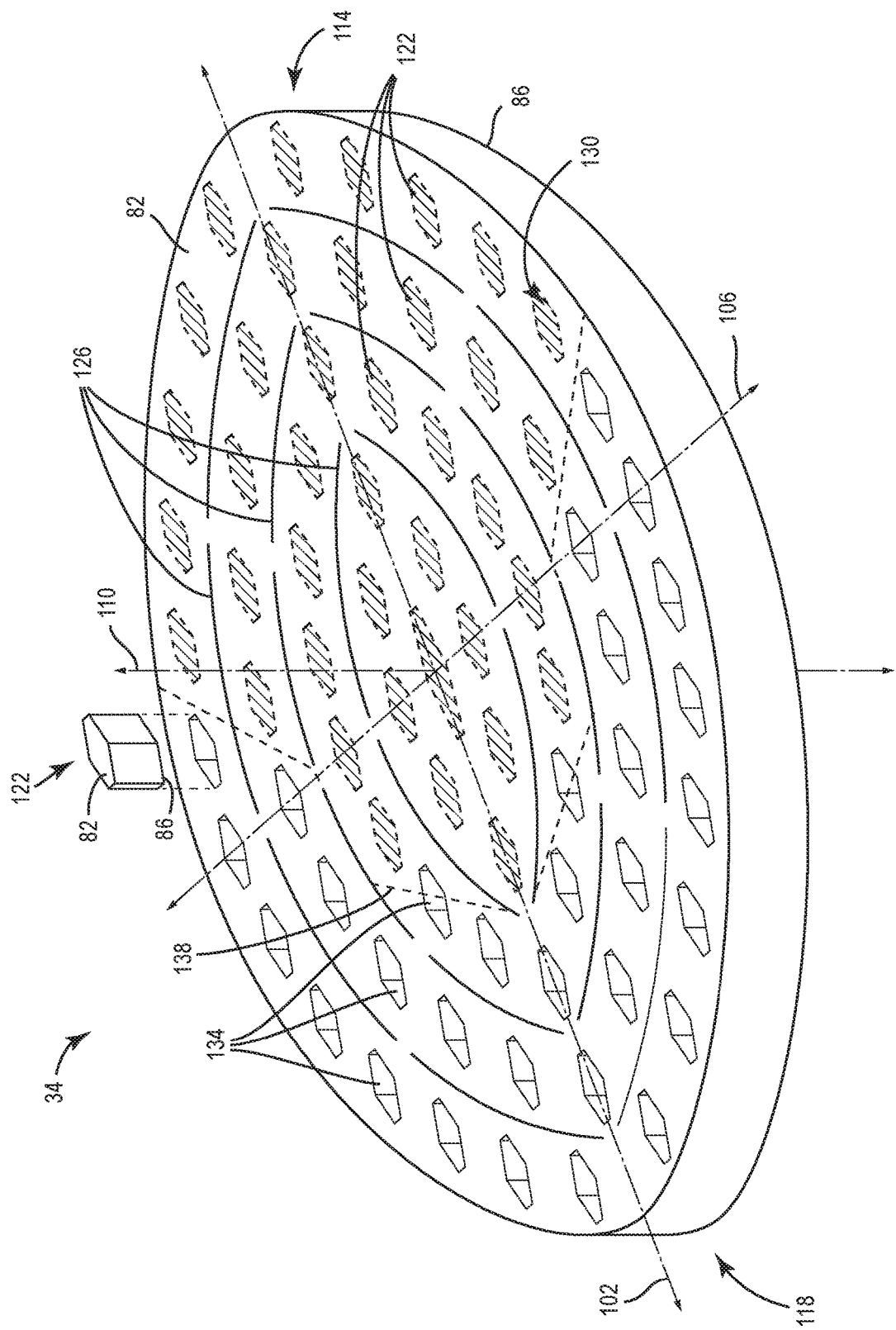
FIG. 3 is perspective view of the abdominal dressing of FIG. 2 including a pattern of voids.

As shown in FIGS. 2-3, the body or compressive component 34 is generally symmetrical and elliptical-shaped. The compressive component 34 includes a first surface 82 and the second, fascia-facing, surface 86 opposite the first surface 82. When the compressive component 34 is applied to a wound, the first surface 82 faces away from the fascia and the second surface faces toward the fascia. In some embodiments, the second surface 86 of the compressive component 34 contacts the first layer 58 of the abdominal treatment device 28. In some embodiments, the first surface of the compressive component 34 contacts the sealing member 38. The compressive component 34 includes a longitudinal axis 102 defining a longitudinal direction, a lateral axis 106 defining a lateral direction, and a vertical axis 110 defining a vertical direction. The compressive component 34 includes a first tapered end 114 and a second tapered end 118. The first tapered end 114 and the second tapered end 118 are spaced part along the longitudinal axis 102. The compressive component 34 is configured to collapse in a first direction while resisting collapse in a second direction that is substantially perpendicular to the first direction. For example, in the illustrated embodiment, the compressive component 34 is configured to collapse in a lateral direction (e.g., along the lateral axis 106) and/or a radial direction (e.g., along the lateral axis 106 and the longitudinal axis 102) under negative pressure while resisting compression in a vertical direction (e.g. along the vertical axis 110) under negative pressure.

The compressive component 34 includes a plurality of removable portions 122 and a plurality of sizing perforations 126. FIG. 2 illustrates the compressive component 34 in which none of the removable portions 122 have been removed. FIG. 3 illustrates the compressive component 34 in which a portion of the removable portions 122 has been removed.

The plurality of removable portions 122 is oriented in a pattern that is generally symmetric with respect to the lateral axis 106 and the longitudinal axis 102. In the illustrated embodiment, the removable portions 122 are hexagons. In other embodiments, the removable portions 122 can be other geometric shapes. Removal of at least one of the plurality of removable portions 122 can increase a lateral and/or a radial force generated as the compressive component 34 collapses under negative pressure. The removable portions 122 include a marking 130 to indicate that the removable portions 122 can be removed from the compressive component 34. In some embodiments, the markings 130 can be colors and/or patterns. In some embodiments, the marking 130 can indicate an increase in the lateral force that is generated upon removal of each of the removable portions 122. The increase in the lateral force that is generated upon removal of each of the removable portions 122 is based on the size of the removable portions 122. Removing at least one of the plurality of removable portions 122 can change a compression profile of the compressive component 34. As used herein, the phrase "compression profile" refers to a shape of the compressive component 34 under negative pressure. Accordingly, removal of a portion of the plurality of removable portions 122 can be used to customize the compression profile of the compressive component 34 to a shape of the wound being treated. For example, FIG. 2 illustrates the compressive component 34 in which none of the plurality of removable portions 122 has been removed. Accordingly, compressive component 34 collapses according to the first compression profile" in the compression of the compressive component 34 under negative pressure is generally symmetric (e.g., uniform) along the lateral axis 106 and the longitudinal axis 102.

By way of non-limiting example, FIG. 3 illustrates the compressive component 34 in which a portion of the removable portions 122 has been removed from the compressive component 34 to form a plurality of through-openings or voids 134 in the compressive component 34. The plurality of voids 134 form a pattern of voids 134 that generates a second compression profile different than the first compression profile. For example, in the configuration of FIG. 3, compression under negative pressure is symmetric with respect to the longitudinal axis 102. Compression under negative pressure is asymmetric with respect to the lateral axis 106. More removable portions 122 have been removed from the compressive component 34 on the left side of the lateral axis 106 than have been on the right side of the lateral axis 106. Accordingly, under negative pressure, the compressive component 34 experiences more lateral compression on the left side of the lateral axis 106 than on the right side of the lateral axis, as is shown by the dashed lines 138. The pattern of formed by the plurality of voids 134 illustrated in FIG. 3 is optimized for closure of a teardrop-shaped fascial incision that is wider at one end than at another end. Accordingly, the compressive component 34 would be oriented on a patient such that the portion of the compressive component 34 that has more intact removable portions 122 is adjacent the wider portion of the incision and the portion of the compressive component 34 that has more voids 134 is over the narrow portion of the incision. The voids 134 facilitate collapse of the compressive component 34 into the teardrop shape under negative pressure, thereby providing uniform closure forces over the fascial incision.

In other configurations, different ones of the plurality of removable portions 122 can be selectively and individually removed to generate different compression profiles in the compressive component 34. For example, in some configurations, the compression profile can include a pattern of voids 134 oriented such that compressive component 34 has a different amount of compression proximate a center of the compressive component than proximate the perimeter of the compressive component 34. The compression profiles can be either be symmetric (e.g., uniform) and/or asymmetric with respect to the longitudinal axis 102 and/or the lateral axis 106.

In some embodiments, the plurality of removable portions 122 are formed by perforations that extend between the first surface 82 and the second surface 86 and surround the removable portions 122. In other embodiments, the plurality of removable portions 122 are cut into the first surface 82 of the compressive component 34. The cuts extend into the compressive component 34 in the vertical direction but do not extend through the second surface 86 of the compressive component 34. In such an embodiment, the uncut portion of the compressive component 34 may extend approximately 1-2 mm in the vertical direction and approximately 2-4 directions in the lateral and/or longitudinal direction. The perforations and/or the cuts are configured so that a force of less than 5N can be used to remove the removable portions 122 from the compressive component 34. In some embodiments, the perforations and/or the cuts can be configured so that there is a higher force required to remove the removable portions from one of the first surface 82 and the second surface 86. For example, the removable portions 122 may require more force from removal from the second surface 86 for compressive components 34 configured for treating wounds in which granulation may occur.

In embodiments in which the compressive component 34 is a foam material, the compressive component 34 may include a welded film layer on one or both of the first surface 82 and the second surface 86. In such embodiments, the film layer may include perforations approximately 3 mm long in the shape of the removable portions 122 and the removable portions 122 may be formed by through-cuts in the compressive component 34, such that the removable portions 122 are held in place by the film layer. In some embodiments, the film layer can be a polyurethane film secured to the foam material with an acrylic adhesive. In other embodiments, the film layer can be Miliken fabric.

With continued reference to FIGS. 2-3, the pattern of sizing perforations 126 includes a plurality of sizing perforations 126 extending between the first surface 82 and the second surface 86. The pattern of sizing perforations 126 includes a first ring of sizing perforations 126, a second ring of sizing perforations 126, and a third ring of sizing perforations 126. The first ring of sizing perforations 126, the second ring of sizing perforations 126, and the third ring of sizing perforations 126 are generally elliptical and generally follow a contour of the compressive component 34. The sizing perforations 126 facilitate removal of a portion of the compressive component 34 to adjust a size of the compressive component 34. The plurality of removable portions 122 is spaced from the plurality of sizing perforations 126. The plurality of sizing perforations 126 facilitate tool-less resizing of the compressive component 34 to conform to a size of the treatment area.

Figure 4:
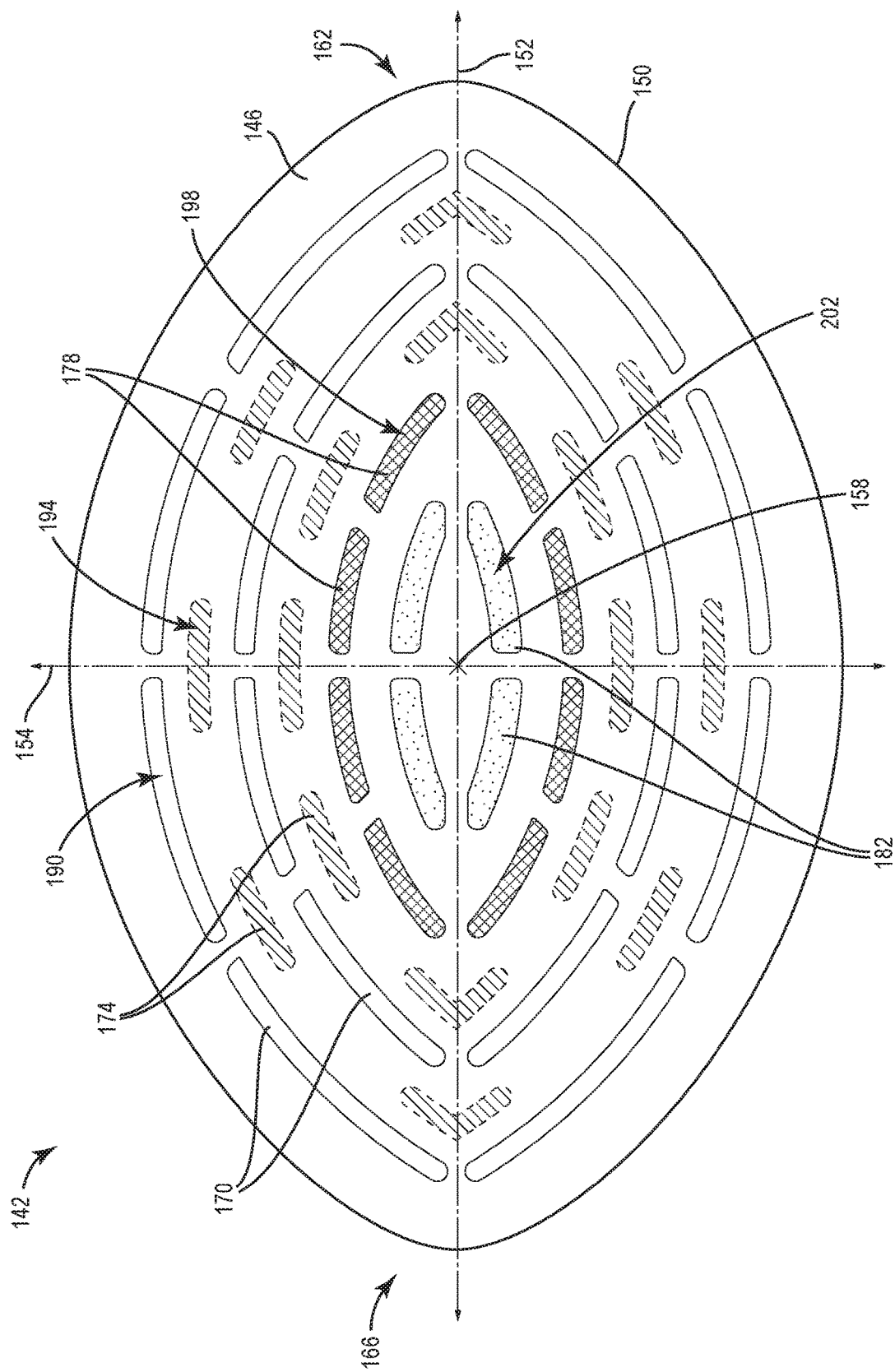
FIG. 4 is a front view of an abdominal dressing for use with the wound therapy system of FIG. 1 according to an exemplary embodiment.

FIG. 4 illustrates a body or compressive component 142 according to another embodiment. The compressive component 142 is generally symmetrical and elliptical-shaped. The compressive component 142 is shown to include a first surface 146 and a second, fascia-facing, surface 150 opposite the first surface 146. When the compressive component 142 is applied to a wound, the first surface 146 faces away from the fascia and the second surface 150 faces toward the fascia. In some embodiments, the second surface 150 of the compressive component 142 contacts the first surface 146 of the abdominal treatment device 28. In some embodiments, the first surface of the compressive component 142 contacts the sealing member 38. The compressive component 142 includes a longitudinal axis 152 defining a longitudinal direction, a lateral axis 154 defining a lateral direction, and a vertical axis 158 defining a vertical direction. The compressive component 142 includes a first tapered end 162 and a second tapered end 166. The first tapered end 162 and the second tapered end 166 are spaced part along the longitudinal axis 152. The compressive component 142 is configured to collapse in a first direction while resisting collapse in a second direction that is substantially perpendicular to the first direction. For example, in the illustrated embodiment, the compressive component 142 is configured to collapse in a lateral direction (e.g., along the lateral axis 154) and/or a radial direction (e.g., along the lateral axis 154 and the longitudinal axis 152) while resisting compression in a vertical direction (e.g., along the vertical axis 158) under negative pressure. The compressive component 142 can be made of the materials described above with respect to the compressive component 34.

The compressive component 142 includes a first plurality of removable portions 170, a second plurality of removable portions 174, a third plurality of removable portions 178, a fourth plurality of removable portions 182. In some embodiments, the compressive component 142 includes a plurality of sizing perforations (not shown). The plurality of sizing perforations are substantially similar to the sizing perforations 126 of the compressive component 34 and will not be described in detail herein for the sake of brevity.

The pluralities of removable portions 170, 174, 178, 182 are arranged in concentric rings and are configured for generally radial compression. The first plurality of removable portions 170 are generally elongate and spaced close together. The second plurality of removable portions 174 are shorter than the first plurality of removable portions 170 and spaced apart by a distance longer than their length. The third plurality of removable portions 178 are substantially similar to the second plurality of removable portions 174 but are spaced close together. The fourth plurality of removable portions 182 are thicker and spaced close together. In other embodiments, the removable portions 170, 174, 178, 182 can be other geometric shapes. Accordingly, removal of each of the pluralities of removable portions 170, 174, 178, 182 can generate a different increase in a lateral and/or a radial force generated as the compressive component 142 collapses under negative pressure. Accordingly, the first plurality of removable portions 170 can have a first marking 190 indicative of a first increase in compressive force, the second plurality of removable portions 174 can have a second marking 194 indicative of a second increase in compressive force, the third plurality of removable portions 178 can have a third marking 198 indicative of a third increase in compressive force, and the fourth plurality of removable portions 182 can have a fourth marking 202 indicative of a fourth increase in compressive force. The markings 190, 194, 198, 202 are substantially similar to the markings 130 described above with respect to the compressive component 34. However, the markings 190, 194, 198, 202 are different from each other to indicate an increase in the lateral force that is generated upon removal of each of the removable portions is different for the first plurality of removable portions 170, the second plurality of removable portions 174, the third plurality of removable portions 178, and the fourth plurality of removable portions 182. As described above with respect to FIGS. 2 and 3, the removable portions 170, 174, 178, 182 can be selectively and individually removed to change the compressive component 142 from having a first compression profile in which none of the removable portions 170, 174, 178, 182 is removed and second compression profile in which at least one of any of the removable portions 170, 174, 178, 182 has been removed.

In some embodiments, the pluralities of removable portions 170, 174, 178, 182 are formed by perforations that extend between the first surface 146 and the second surface 150 and surround the pluralities of removable portions 170, 174, 178, 182. In other embodiments, the pluralities of removable portions 170, 174, 178, 182 are cut into the first surface 146 of the compressive component 142. The perforations and/or cuts are substantially similar to the perforations and/or cuts described above with respect to the compressive component 34 and will not be discussed in detail herein for the sake of brevity.

Although the removable portions 122 of the compressive component 142 and the removable portions 170, 174, 178, 182 of the compressive component are configured for toolless removal, in some embodiments, removal of the removable portions 170, 174, 178, 182, may be facilitated by a tool having a similar cross-sectional shape as the removable portions 170, 174, 178, 182.

While the compressive components 34, 142 are described in the context of the wound therapy system 10 configured for treatment of deep abdominal wounds, this description is intended to be non-limiting. The compressive components 34, 142 can have other shapes and can be used to treat other types of wounds.

Deployment of the Compressive Component

In operation, the user selects the compressive component 34 and compares a length of the compressive component 34 in the generally longitudinal direction to a length of the fascial incision. The user may tear the compressive component 34 along the perforations 126 to size compressive component 34 such that the length of the compressive component 34 in the generally longitudinal direction is substantially similar to the length of the fascial incision. Next, the user may remove a portion of the plurality of removable portions 122 from the compressive component 34 to form the plurality of voids 134. The step of removing at least one of the plurality of removable portions 122 from the compressive component 34 transforms a compressive profile of the compressive component 34 from the first compressive profile to the second compressive profile based on a shape of the fascial incision. The user may determine which of the plurality of removable portions 122 to remove from the compressive component 34 based on the shape of the fascial incision and/or the marking 130 indicative of an increase in lateral force generated by removing each of the removable portions 122 including the marking 130 from the compressive component 34. In some configurations, the second compressive profile can be symmetric (e.g., uniform) about at least one of the longitudinal axis 102 and the lateral axis 106. In other configurations, the second compressive profile can be asymmetric (e.g., non-uniform) with respect to both the longitudinal axis 102 and the lateral axis 106. The user then positions the compressive component 34 in the abdominal cavity such that the longitudinal axis 102 is generally aligned with the fascial incision. The user applies negative pressure to the compressive component 34 using the NPWT system 26 to provide negative pressure to the wound dressing 14 to compress the compressive component 34.

The compressive component 142 may be resized as described above with respect to the compressive component 34. The pluralities of removable portions 170, 174, 178, 182 may be selectively removed from the compressive component 142 to transform the compressive profile of the compressive component 142 from the first compressive profile to the second compressive profile as described above with respect to the compressive component 34.

Composite Compressive Component

Figure 5:
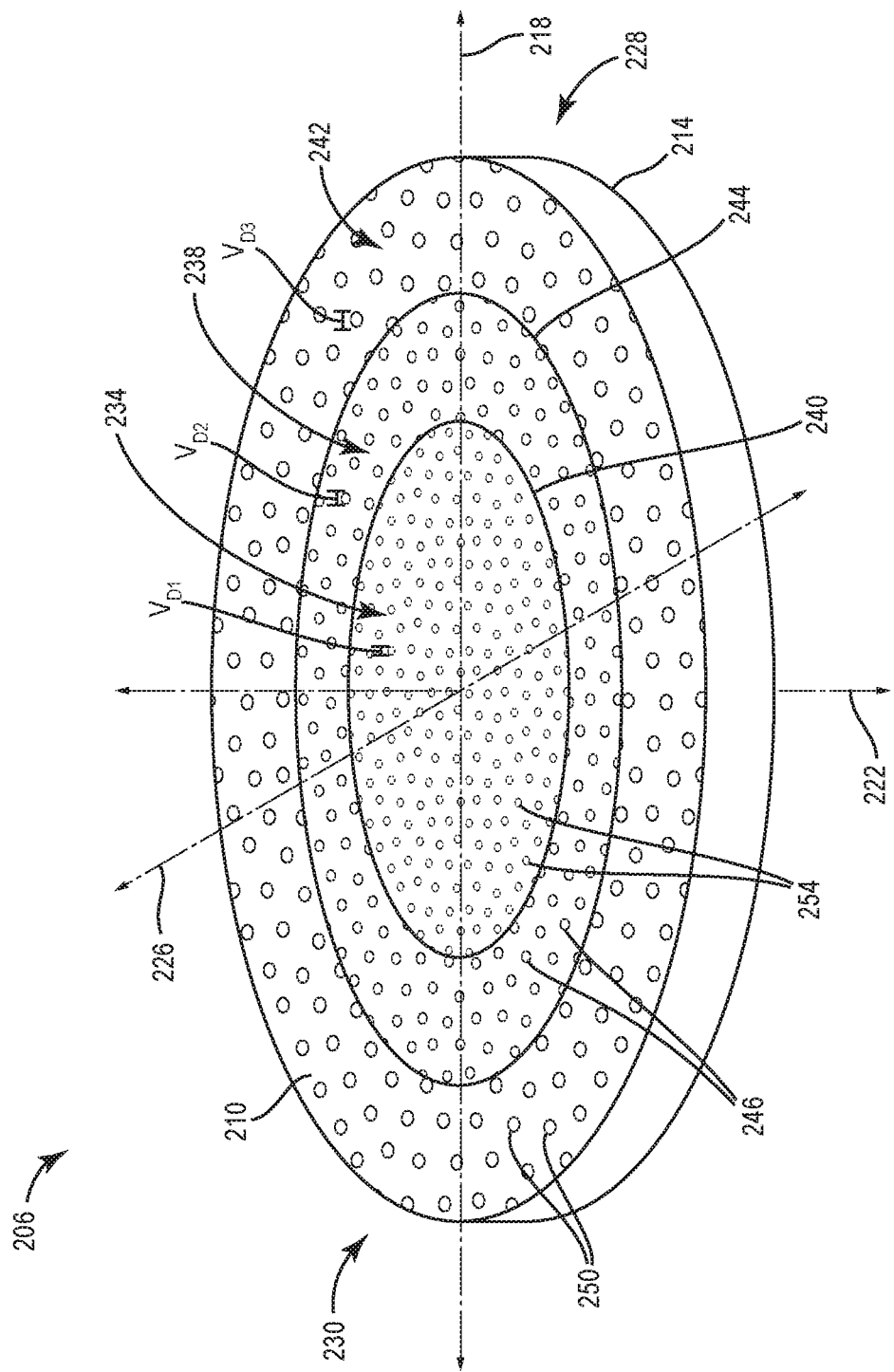
FIG. 5 is a perspective view of a composite abdominal dressing for use with the wound therapy system of FIG. 1 according to an exemplary embodiment.

FIG. 5 illustrates a composite body or compressive component 206 according to an exemplary embodiment. The composite compressive component 206 is generally symmetrical and elliptical-shaped. The composite compressive component 206 includes a first surface 210 and a second, fascia-facing, surface 214. In some embodiments, the second surface 214 of the composite compressive component 206 contacts the first layer 58 of the abdominal treatment device 28. In some embodiments, the first surface 210 of the composite compressive component 206 contacts the sealing member 38. The composite compressive component 206 includes a longitudinal axis 218 defining a longitudinal direction, a lateral axis 222 defining a lateral direction, and a vertical axis 226 defining a vertical direction. The composite compressive component 206 includes a first tapered end 228 and a second tapered end 230. The first tapered end 228 and the second tapered end 230 are spaced apart along the longitudinal axis 218. The composite compressive component 206 is configured to collapse in a first direction while resisting collapse in a second direction that is substantially perpendicular to the first direction. For example, in the illustrated embodiment, the composite compressive component 206 is configured to collapse in a lateral direction (e.g., along the lateral axis 222) and/or a radial direction (e.g., along the lateral axis 222 and the longitudinal axis 218) while resisting compression in a vertical direction (e.g., along the vertical axis 226) under negative pressure.

The composite compressive component 206 includes a first concentric segment 234, a second concentric segment 238, and a third concentric segment 242. The first concentric segment 234 forms a central portion of the composite compressive component 206. The second concentric segment 238 is substantially ring-shaped and includes a through-opening 240 sized to receive the first concentric segment 234. The third concentric segment 242 is substantially ring-shaped and includes a through-opening 244 for receiving the second concentric segment 238. Accordingly, the first concentric segment 234, the second concentric segment 238, and the third concentric segment 242 are arranged in a nested configuration. While the composite compressive component 206 illustrated in FIGS. 5-6 includes three concentric segments, in other embodiments, the compressive component 206 can include more or fewer concentric segments.

In the illustrated embodiment, the first concentric segment 234, the second concentric segment 238, and the third concentric segment 242 are formed of the same compressive material. The compressive material can be any of the materials discussed above with respect to the compressive component 34. In some embodiments, the compressive material is Granufoam® or a felted foam material. The first concentric segment 234 includes a first plurality of voids 246 that generate a first compression ratio. As used herein, "compression ratio" is the ratio of the change in length in a lateral direction under negative pressure to the uncompressed length in the lateral direction. The first plurality of voids 246 have a diameter $VD_1$ of approximately 1-2 mm. The first plurality of voids 246 are spaced close together. In the illustrated embodiment, the first plurality of voids 246 are generally circular in cross-section. In other embodiments, the first plurality of voids 246 can have other cross-sectional shapes, such as oval, hexagonal, rectangular, and any other geometric shape. The second concentric segment 238 includes a second plurality of voids 250 that generate a second compression ratio that is larger than the first compression ratio. The second plurality of voids 250 have a diameter $VD_2$ of approximately 2-4 mm. The second plurality of voids 250 are spaced farther apart than the first plurality of voids 246. In the illustrated embodiment, the second plurality of voids 250 are generally circular in cross-section. In other embodiments, the second plurality of voids 250 can have other cross-sectional shapes, such as oval, hexagonal, rectangular, and any other geometric shape. The third concentric segment 242 includes a third plurality of voids 254 that generate a third compression ratio that is larger than the second compression ratio and the first compression ratio. The third plurality of voids 254 have a diameter $VD_3$ of approximately 6-8 mm. The third plurality of voids 254 are spaced farther apart than the first plurality of voids 246 and the second plurality of voids 250. In the illustrated embodiment, the third plurality of voids 254 are generally circular in cross-section. In other embodiments, the third plurality of voids 254 can have other cross-sectional shapes, such as oval, hexagonal, rectangular, and any other geometric shape. The first plurality of voids 246, the second plurality of voids 250, and the third plurality of voids 254 are configured to change the density of the compressive material. Accordingly, under negative pressure, the third concentric segment 242 has high collapse, the second concentric segment 238 has intermediate collapse, and the first concentric segment 234 has low collapse.

Figure 6:
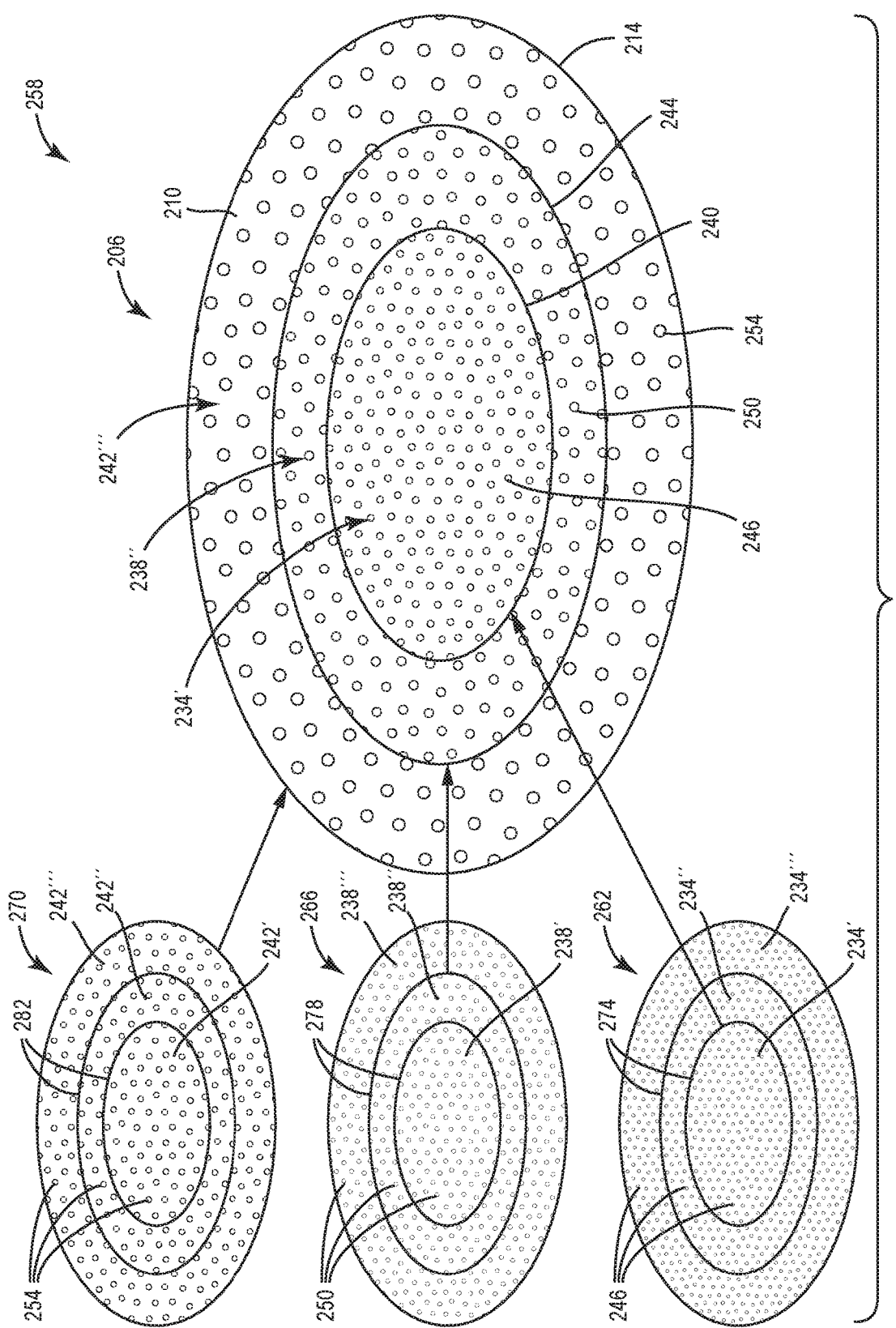
FIG. 6 is front view of a composite abdominal dressing system for use with the composite abdominal dressing of FIG. 5.

FIG. 6 illustrates a system 258 for forming the composite compressive component 206 according to an exemplary embodiment. The system includes a first pad 262 of the compressive material including the first plurality of voids 246, a second pad 266 of the compressive material including the second plurality of voids 250, and a third pad 270 of the compressive material including the third plurality of voids 254. In the illustrated embodiment, the first plurality of voids 246, the second plurality of voids 250, and the third plurality of voids 254 are evenly distributed over the first pad 262, the second pad 266, and the third pad 270. In other embodiments, the first plurality of voids 246, the second plurality of voids 250, and the third plurality of voids 255 may be arranged in different patterns and/or may be unevenly distributed over the first pad 262, the second pad 266, and the third pad 270 to change a compressive profile of the composite compressive component 206 formed from at least two of the first pad 262, the second pad 266, and the third pad 270. The first pad 262 includes a first plurality of sizing perforations 274 that divide the first pad 262 into a first plurality of concentric segments 234. The second pad 266 includes a second plurality of sizing perforations 278 that divide the second pad 266 into a second plurality of concentric segments 238. The third pad 270 includes a third plurality of sizing perforations 282 that divide the third pad 270 into a third plurality of concentric segments 242. In the illustrated embodiment, the first plurality of sizing perforations 274, the second plurality of sizing perforations 278, and the third plurality of sizing perforations 282 include two generally elliptical rings of perforations that divide the first pad 262 into three concentric segments. In other embodiments, the first plurality of sizing perforations 274, the second plurality of sizing perforations 278, and the third plurality of sizing perforations 282 may include more or fewer rings of perforations that divide the first pad 262, the second pad 266, and the third pad 270 into more or fewer segments. For example, in some embodiments, the first pad 262, the second pad 266, and the third pad 270 may include 2 concentric segments or 4 concentric segments. In the illustrated embodiment, the first plurality of sizing perforations 274, the second plurality of sizing perforations 278, and the third plurality of sizing perforations 282 have substantially the same dimensions such that the first plurality of concentric segments 234, the second plurality of concentric segments 238, and the third plurality of concentric segments 242 can be used to form the composite compressive component 206 in any order. Accordingly, the composite compressive component 206 is formed by combining concentric segments from the first pad 262, the second pad 266, and the third pad 270. For any of the pads 262, 266, 270 described herein, the prime "'" symbol refers to a first concentric segment, the double prime "''" symbol refers to a second concentric segment, and the triple prime "'''" symbol refers to a third concentric segment. In some embodiments, the first pad 262, the second pad 266, and the third pad 270 may have different colors or patterns to indicate that the first pad 262, the second pad 266, and the third pad 270 have different compression ratios. The sizing perforations 274, 278, 282 are spaced from the pluralities of voids 246, 250, 254.

For example, to form the composite compressive component 206 configured for high, rapid compression proximate a perimeter of the composite compressive component 206, an intermediate amount of compression adjacent the high compression portion of the composite compressive component 206, and low compression proximate a center of the composite compressive component 206, a user may remove the smallest concentric segment 234' of the first pad 262. The user may then remove the concentric segment 238'' from the second pad 266 and remove the concentric segment 238' from the second pad 266 to form a through-opening in the second pad 266. Since the first plurality of sizing perforations 274 and the second plurality of sizing perforations 278 are substantially the same, the user can position the concentric segment 234' from the first pad 262 into the through-opening 240 in the concentric segment 238'' from the second pad 266. The concentric segment 234' may fit in the through-opening 240 of the concentric segment 238'' in a friction fit. The user may then remove a concentric segment 242''' from the third pad 270 that is larger than the concentric segment 238''. The user then may remove the concentric segments 242', 242'' from the concentric segment 242''' to form the through-opening 244 in the concentric segment 242'' of the third pad 270. Since the second plurality of sizing perforations 278 and the third plurality of sizing perforations 282 are substantially the same, the user can position the concentric segment 238'' into the through-opening to form the composite compressive component 206. The concentric segment 238" may fit in the through-opening 240 of the concentric segment 242'" in a friction fit. In some embodiments, concentric segments may be cut to form combined segments made from different pads to form a composite pad having an asymmetrical compressive profile.

FIGS. 7-9 illustrate a composite body or composite compressive component 286 and a system 290 for forming the composite compressive component 286 according to an exemplary embodiment. The composite compressive component 286 is generally symmetrical and elliptical-shaped. The composite compressive component 286 includes a first surface 294 and a second, fascia-facing, surface 298. In some embodiments, the second surface 298 of the composite compressive component 286 contacts the first layer 58 of the abdominal treatment device 28. In some embodiments, the first surface 294 of the composite compressive component 286 contacts the sealing member 38. The composite compressive component 286 includes a longitudinal axis 302 defining a longitudinal direction, a lateral axis 306 defining a lateral direction, and a vertical axis 310 defining a vertical direction. The composite compressive component 286 includes a first tapered end 314 and a second tapered end 318. The first tapered end 314 and the second tapered end 318 are spaced apart along the longitudinal axis 302. The composite compressive component 286 is configured to collapse in a first direction while resisting collapse in a second direction that is substantially perpendicular to the first direction. For example, in the illustrated embodiment, the composite compressive component 286 is configured to collapse in a lateral direction (e.g., along the lateral axis 306) and/or a radial direction (e.g., along the lateral axis 306 and the longitudinal axis 302) while resisting compression in a vertical direction (e.g., along the vertical axis 310) under negative pressure.

FIG. 7 illustrates a system 290 for forming the composite compressive component 286 according to an exemplary embodiment. The system includes a first pad 322, a second pad 326, and a third pad 330. The first pad 322 is a first compressive material having first material properties that generate a first compression ratio. The second pad 326 is a second compressive material having second material properties that generate a second compression ratio that is higher than the first compression ratio. The third pad 330 is a third compressive material having third material properties that generate a third compression ratio that is higher than the first compression ratio and the second compression ratio. The first material properties, the second material properties, and the third material properties may be material properties that determine a density of the first compressive material, the second compressive material, and the third compressive material, respectively. The first density is higher than the second density and the second density is higher than the third density. In some embodiments, the first material properties, the second material properties, and the third material properties can include at least one of a concentration of pores per inch ("PPI"), a density, and a percent felting. At least a portion of the first material properties, the second material properties, and third material properties are different. The first compressive material, the second compressive material, and the third compressive material can be any of the materials discussed above with respect to the compressive component 34. In some embodiments, at least one of the first compressive material, the second compressive material, and the third compressive material is Granufoam® or a felted foam material. In some embodiments, at least one of the first compressive material, the second compressive mate-rial, and the third compressive material is a three-dimensional textile material such as BallTex.

The first pad 322 includes a first plurality of sizing perforations 334 that divide the first pad 322 into a first plurality of concentric segments 338. The second pad 326 includes a second plurality of sizing perforations 342 that divide the second pad 326 into a second plurality of concentric segments 346. The third pad 330 includes a third plurality of sizing perforations 350 that divide the third pad 330 into a third plurality of concentric segments 354.

In the illustrated embodiment, the first plurality of sizing perforations 334, the second plurality of sizing perforations 342, and the third plurality of sizing perforations 350 include two generally elliptical rings of perforations that divide the first pad 322, the second pad 326, and the third pad 330 into three concentric segments. In other embodiments, the first plurality of sizing perforations 334, the second plurality of sizing perforations 342, and the third plurality of sizing perforations 350 may include more or fewer rings of perforations that divide the first pad 322, the second pad 326, and the third pad 330 into more or fewer segments. For example, in some embodiments, the first pad 322, the second pad 326, and the third pad 330 may include 2 concentric segments or 4 concentric segments. In the illustrated embodiment, the first plurality of sizing perforations 334, the second plurality of sizing perforations 342, and the third plurality of sizing perforations 350 have substantially the same dimensions such that the first plurality of concentric segments 338, the second plurality of concentric segments 346, and the third plurality of concentric segments 354 can be used to form the composite compressive component 286 in any order. Accordingly, the composite compressive component 286 is formed by combining concentric segments from the first pad 322, the second pad 326, and the third pad 330. For any of the pads 322, 326, 330 described herein, the prime "'" symbol refers to a first concentric segment, the double prime "''" symbol refers to a second concentric segment, and the triple prime "'''" symbol refers to a third concentric segment. In some embodiments, the first pad 322, the second pad 326, and the third pad 330 may have different colors or patterns to indicate that the first pad 322, the second pad 326, and the third pad 330 have different compression ratios.

To form a composite compressive component 286 that is configured for high, rapid compression proximate a perimeter of the composite compressive component 286, an intermediate amount of compression adjacent the high compression portion of the composite compressive component 286, and low compression proximate a center of the composite compressive component 286, a user may remove the smallest concentric segment 338' of the first pad 322. The user may then remove the concentric segment 346" from the second pad 326 and remove the concentric segment 346' from the second pad 326 to form a through-opening 358 in the second pad 326. Since the first plurality of sizing perforations 334 and the second plurality of sizing perforations 342 are substantially the same, the user can position the concentric segment 338' from the first pad 322 into the through-opening 358 in the concentric segment 346" from the second pad 326. The concentric segment 338' may fit in the through-opening 358 of the concentric segment 346" in a friction fit. The user may then remove a concentric segment 354'" from the third pad 330 that is larger than the concentric segment 346". The user then may remove the concentric segments 346', 346" from the concentric segment 346'" to form a through-opening 362 in the concentric segment 354'" of the third pad 330. Since the second plurality of sizing perforations 342 and the third plurality of sizing perforations 350 are substantially the same, the user can position the concentric segment 346" (and the concentric segment 338') into the through-opening 362 to form the composite compressive component 286. The concentric segment 346" may fit in the through-opening 362 of the concentric segment 354''' in a friction fit.

FIG. 8 illustrates a perspective view of the composite compressive component 286 under ambient pressure conditions and FIG. 9 is a perspective view of the composite compressive component under negative pressure conditions according to an exemplary embodiment. The composite compressive component 286 includes the concentric segment 338' of the first compressive material, the second concentric segment 346" of the second compressive material, and the third concentric segment 354''' of the third compressive material. The first concentric segment 338' forms a central portion of the composite compressive component 286. The second concentric segment 346" is substantially ring-shaped and includes the through-opening 358 sized to receive the first concentric segment 338'. The third concentric segment 354'' is substantially ring-shaped and includes the through-opening 362 for receiving the second concentric segment 346". Accordingly, the first concentric segment 338', the second concentric segment 346", and the third concentric segment 354''' are arranged in a nested configuration. As is apparent from comparing FIGS. 8 and 9, the composite compressive component 286 has compressed in a generally lateral direction and a generally vertical direction as a under negative pressure conditions. As shown in FIG. 9, under negative pressure, the third concentric segment 354''' has high collapse in the generally lateral direction, the second concentric segment 346" has intermediate collapse in the generally lateral direction, and the first concentric segment 338' has low collapse in the generally lateral direction.

Although the system 258 for forming the composite compressive component 206 and the system 290 for forming the composite compressive component 286 are illustrated using three pads having three concentric segments, in other embodiments, the system 258 and the system 290 can include more or fewer pads and/or more or fewer concentric segments. In the illustrated embodiments, the sizing perforations are generally elliptical. In other embodiments, the pluralities of sizing perforations may have different shapes than the sizing perforations illustrated in FIGS. 6-9. Although FIGS. 6-9 illustrate one compressive segment from each of the compressive pads, in some embodiments, more or fewer compressive segments from each of the compressive pads may be used. Furthermore, the compressive segments can be arranged in any order to provide a desired compressive profile based on the wound being treated. While the composite compressive component 286 illustrated in FIGS. 7-9 includes three concentric segments, in other embodiments, the compressive component 286 can include more or fewer concentric segments. In some embodiments, concentric segments may be cut to form combined segments made from different pads to form a composite pad having an asymmetrical compressive profile.

While the composite compressive components 206, 286 are described in the context of the wound therapy system 10 configured for treatment of deep abdominal wounds, this description is intended to be non-limiting. The composite compressive components 206, 286 can have other shapes and can be used to treat other types of wounds.

CONFIGURATION OF EXEMPLARY EMBODIMENTS

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

What is claimed is:

1. A negative pressure wound therapy (NPWT) device for a deep abdominal wound, the NPWT device comprising:
a body comprising a porous material having a first compressive profile, the body including a plurality of removable portions supported by a substrate portion of the body, wherein each of the plurality of removable portions are individually surrounded by perforations or cuts in the substrate portion of the body such that the substrate portion of the body separates and surrounds the plurality of removable portions, none of the removable portions being surrounded by the perforations or cuts defining another of the removable portions, the substrate portion defining a free perimeter which surrounds all of the plurality of removable portions, each of the removable portions configured to define a void surrounded by the substrate portion of the body when removed, the plurality of removable portions configured to be selectively removed to form a pattern of voids within the substrate to transform the first compressive profile of the body into a second compressive profile based on the pattern of voids.

2. The NPWT device of claim 1, wherein the first compressive profile is symmetric along a lateral axis and a longitudinal axis of the body, and wherein the second compressive profile is asymmetric across at least one of the lateral axis or the longitudinal axis.

3. The NPWT device of claim 1, wherein the second compressive profile is different from the first compressive profile.

4. The NPWT device of claim 1, wherein the plurality of removable portions include markings configured to indicate an increase in compressive force upon removal, at least one of the removable portions marked with a greater increase in compressive force than another of the removable portions.

5. The NPWT device of claim 1, wherein the plurality of removable portions includes:
a first plurality of removable portions having a first shape, the first plurality of removable portions including a first marking configured to indicate a first amount of change in the second compressive profile upon removal of each one of the first plurality of removable portions; and
a second plurality of removable portions having a second shape different than the first shape, the second plurality of removable portions including a second marking configured to indicate a second amount of change in the second compressive profile upon removal of each one of the second plurality of removable portions;

wherein the second amount of change is greater than the first amount of change.

6. The NPWT device of claim 1, wherein the body includes a first surface and a second surface, and wherein a fluid-impermeable layer is secured to the second surface and configured to face a fascia.

7. The NPWT device of claim 1, wherein the body further comprises at least one plurality of sizing perforations that are spaced apart from the removable portions and follow a contour of the body.

8. The NPWT device of claim 1, wherein the body is configured to compress in a first direction under negative pressure, and resist compression in a second direction perpendicular to the first direction under negative pressure.

* * * * *